US006721599B2

(12) United States Patent
de Vries

(10) Patent No.: US 6,721,599 B2
(45) Date of Patent: Apr. 13, 2004

(54) PACEMAKER WITH SUDDEN RATE DROP DETECTION BASED ON QT VARIATIONS

(75) Inventor: Bernhard de Vries, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 175 days.

(21) Appl. No.: 09/987,778

(22) Filed: Nov. 16, 2001

(65) Prior Publication Data
US 2003/0100927 A1 May 29, 2003

(51) Int. Cl.[7] .............................................. A61N 1/365
(52) U.S. Cl. ......................................................... 607/25
(58) Field of Search ...................................... 607/9–25

(56) References Cited

U.S. PATENT DOCUMENTS

| | | |
|---|---|---|
| 4,228,803 A | 10/1980 | Rickards |
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson et al. |
| 4,556,063 A | 12/1985 | Thompson et al. |
| 4,577,633 A | 3/1986 | Bekovits et al. |
| 4,587,970 A | 5/1986 | Holley et al. |
| 4,726,380 A | 2/1988 | Vollmann et al. |
| 4,727,877 A | 3/1988 | Kallok |
| 4,800,883 A | 1/1989 | Winstrom |
| 4,821,723 A | 4/1989 | Baker et al. |
| 4,880,005 A | 11/1989 | Pless et al. |
| 4,949,719 A | 8/1990 | Pless et al. |
| 4,953,551 A | 9/1990 | Mehra et al. |
| 4,972,834 A | 11/1990 | Begemann et al. |
| 5,099,838 A | 3/1992 | Bardy |
| 5,117,824 A | 6/1992 | Keimel et al. |
| 5,131,388 A | 7/1992 | Pless |
| 5,144,949 A | 9/1992 | Olson |
| 5,158,078 A | 10/1992 | Bennet et al. |
| 5,159,428 A | 10/1992 | Rao et al. |
| 5,163,427 A | 11/1992 | Keimel |
| 5,207,218 A | 5/1993 | Carpentier et al. |
| 5,269,298 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennet et al. |
| 5,419,338 A | 5/1995 | Sarma et al. |
| 5,560,368 A | 10/1996 | Berger |
| 5,690,686 A | 11/1997 | Min et al. |
| 5,800,465 A | 9/1998 | Thompson et al. |
| 5,919,210 A | 7/1999 | Lurie et al. |
| 5,991,659 A | 11/1999 | De Vies et al. |
| 6,035,233 A | 3/2000 | Schroeppel et al. |
| 6,070,100 A | 5/2000 | Bakels et al. |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp. 167–170.

"Patients who remained symptomatic after head–up tilt testing" PACE, vol. 16, Apr. 1993, Part II, Abstract #48.

Paradoxical Failure of QT prolongation during cardio inhibitory neurocardiogenic syncope, Am. J. Cardiology, P.100, Jan. 1997.

Primary Examiner—Scott Getzow
(74) Attorney, Agent, or Firm—Girma Wolde-Michael

(57) ABSTRACT

The invention provides an implantable medical device system and method for determining when a patient is undergoing a sudden rate drop (SRD) that should be treated by intervention therapy. Two SRD detection algorithms are provided. A first algorithm is a rate-based algorithm that looks for rate drops that meet stored SRD criteria, and a second algorithm is a QT-based algorithm that detects when QT variations meet criteria that are associated with rate changes characteristic of onset of NMS. The system provides for a plurality of different intervention pacing therapies that are selected based on which detection algorithm, or both algorithms, indicate SRD. The priority of choice of algorithms is programmable.

53 Claims, 9 Drawing Sheets

PACEMAKER WITH SUDDEN RATE DROP DETECTION BASED ON QT VARIATIONS

FIELD OF THE INVENTION

This invention lies in the field of cardiac pacing systems and methods and, more particularly, dual chamber pacing systems that detect a sudden drop in the patient's spontaneous heart rate throughout the heart rate spectrum and provide intervention pacing when such sudden heart rate drop is detected.

BACKGROUND OF THE INVENTION

It is well known that certain patients experience loss of consciousness due to a sudden drop in heart rate, which can be associated with a form of syncope. In many such patients, intervention by pacing may be beneficial for treating the symptoms. Many programmable pacemaker systems, particular dual chamber systems, have incorporated the capability of sudden rate drop (SRD) detection and responsive intervention pacing, frequently with the goal of maintaining AV synchrony as much as possible. An example of such a pacing system that provides improved sudden rate drop detection over the full range of physiological rates is found in U.S. Pat. No. 5,991,659, incorporated herein by reference in its entirety. This system, as is the case generally with other rate drop detection systems in the pacing field, relies solely on analysis of rate changes.

It is known that QT interval, being the time between contraction and repolarization, generally decreases non-linearly with heart rate and, conversely, increases with the RR heartbeat interval. Variation of the QT interval with the RR interval is generally described as having two components. A first component simply accompanies the RR interval, such that an increased RR interval results in a substantially linear lengthening of all parts of the heartbeat, including the QT interval ("QT", or "QT_int"), and vice versa. A second component of QT variation derives from the autonomic control of the heart, leading to an overall non-linear variation of QT with heart rate, as is well documented. Generally, the contribution of autonomic modulation is greater when the heart rate is higher or increasing. For most patients, the variation of QT with rate, i.e., the QT(RR) curve, remains chronically the same. However, there are certain patients in whom changes in their QT(RR) curve occur, which changes can reliably indicate syncope or other cardiac conditions. For example, in patients with evolving neurally-mediated syncope (NMS), the normal QT vs. cycle length relation, or QT(RR), is known to change. Specifically, it has been shown that such patients exhibit a significant shortening of QTc (defined as QT√RR) at rates near the rest rate, meaning that QT does not prolong in a normal fashion as heartbeat interval lengthens. As discussed in PACE, Volume 16, April 1993, Part II, Abstract #48, in patients who remained asymptomatic after head-up tilt testing, QT exhibited appropriate cycle length dependence, while QTc remained essentially unchanged. In patients who were symptomatic after head-up tilt testing, QT exhibited relatively modest prolongation, while QTc shortened significantly. See also Paradoxical Failure of QT Prolongation During Cardioinhibitory Neurocardiogenic Syncope, Am. J. Cardiology, p 100, January 1997. QT is thus a significant parameter for tracing certain variations in cardiac condition. The following patent references set forth in Table 1 suggest techniques for measuring QT for diagnostic purposes.

TABLE 1

| U.S. Pat. No. | Inventor(s) | Issue Date |
|---|---|---|
| 5,991,659 | DeVries et al | Nov. 23, 1999 |
| 5,419,338 | Sarma et al | May 30, 1995 |
| 5,919,210 | Lurie et al | Jul. 6, 1999 |
| 5,560,368 | Berger | Oct. 1, 1996 |

All patents listed in Table 1 are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the present invention.

While several approaches have been made in an effort to utilize QT for diagnostic purposes, there remains a need in the pacemaker art for a device that can efficiently and reliably detect SRD, utilizing both rate change data and QT data. Algorithms that analyze rate change data may be well tuned for some patients, but not others. There thus is a need to supplement such SRD algorithms with additional data, and to provide dual checks in order to validate SRD detection. Upon detection of SRD, the implantable cardiac device can initiate an appropriate pacing intervention.

SUMMARY OF THE INVENTION

It is an object of this invention to provide a cardiac device system and method for Sudden Rate Drop detection that is based both on continuous analysis of cardiac rate changes and continuous analysis of changes in a measure of QT. The object is to provide for sudden rate drop detection throughout the patient's likely rate range, and to provide dual tests, or checks, to determine SRD for patients susceptible to NMS. It is another object to initiate an intervention therapy as soon as possible, and to provide for a programmable choice of what intervention therapy is to be automatically performed.

In accord with the above objects, there is provided a pacemaker system having dual algorithms for detecting the onset of SRD. A first algorithm continuously monitors changes in rate, and is exemplified by the SRD algorithm disclosed in U.S. Pat. No. 5,991,659, de Vries et al, which is incorporated herein by reference in its entirety. A second algorithm is based upon examination of changes in a measure of QT interval of such a nature that suggest the onset of NMS. In a preferred embodiment, the QT algorithm monitors differential changes in QTc, and indicates a detection of SRD when such differentials meet predetermined criteria.

The system and method of this invention further provide for a selection of one of two or more intervention therapies, depending upon whether SRD has been detected on the basis of rate changes, QT changes or both. The system provides for the physician attending the patient to program which interventions are selected and under what conditions. Thus, the physician may select a first intervention therapy in the event of SRD detection based on rate changes alone or QT changes alone, and a second intervention therapy when SRD is detected based both on rate and QT changes.

DESCRIPTION OF THE PREFERRED EMBODIMENTS

Figure 1:
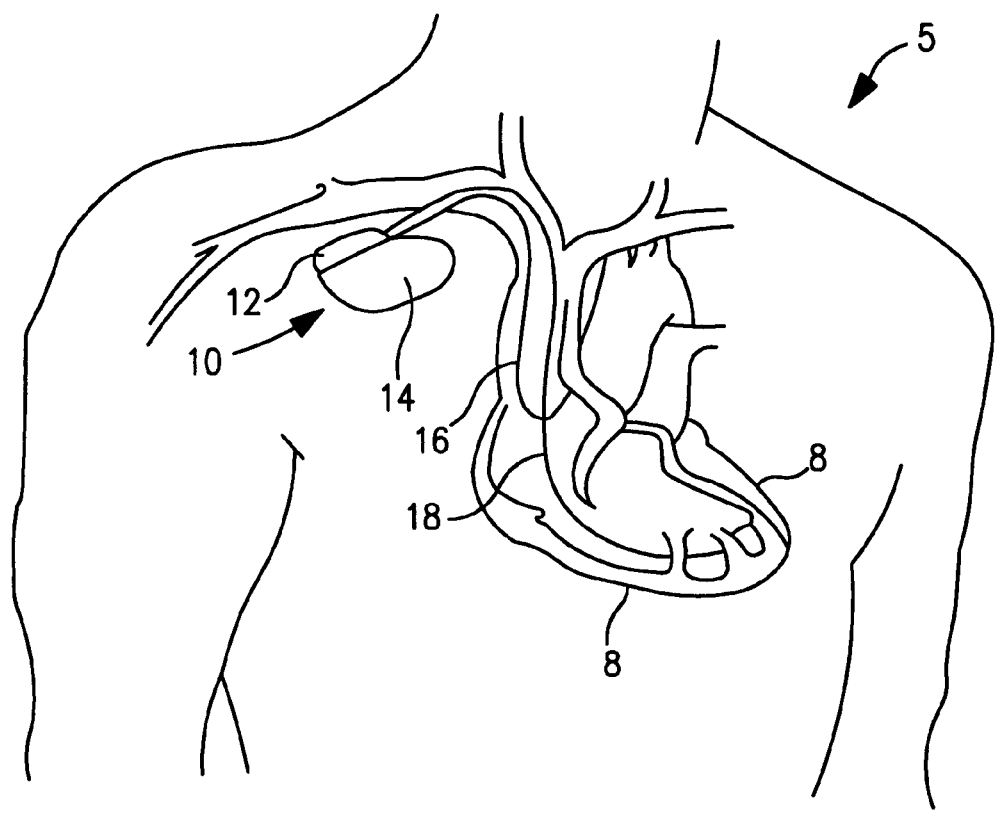
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
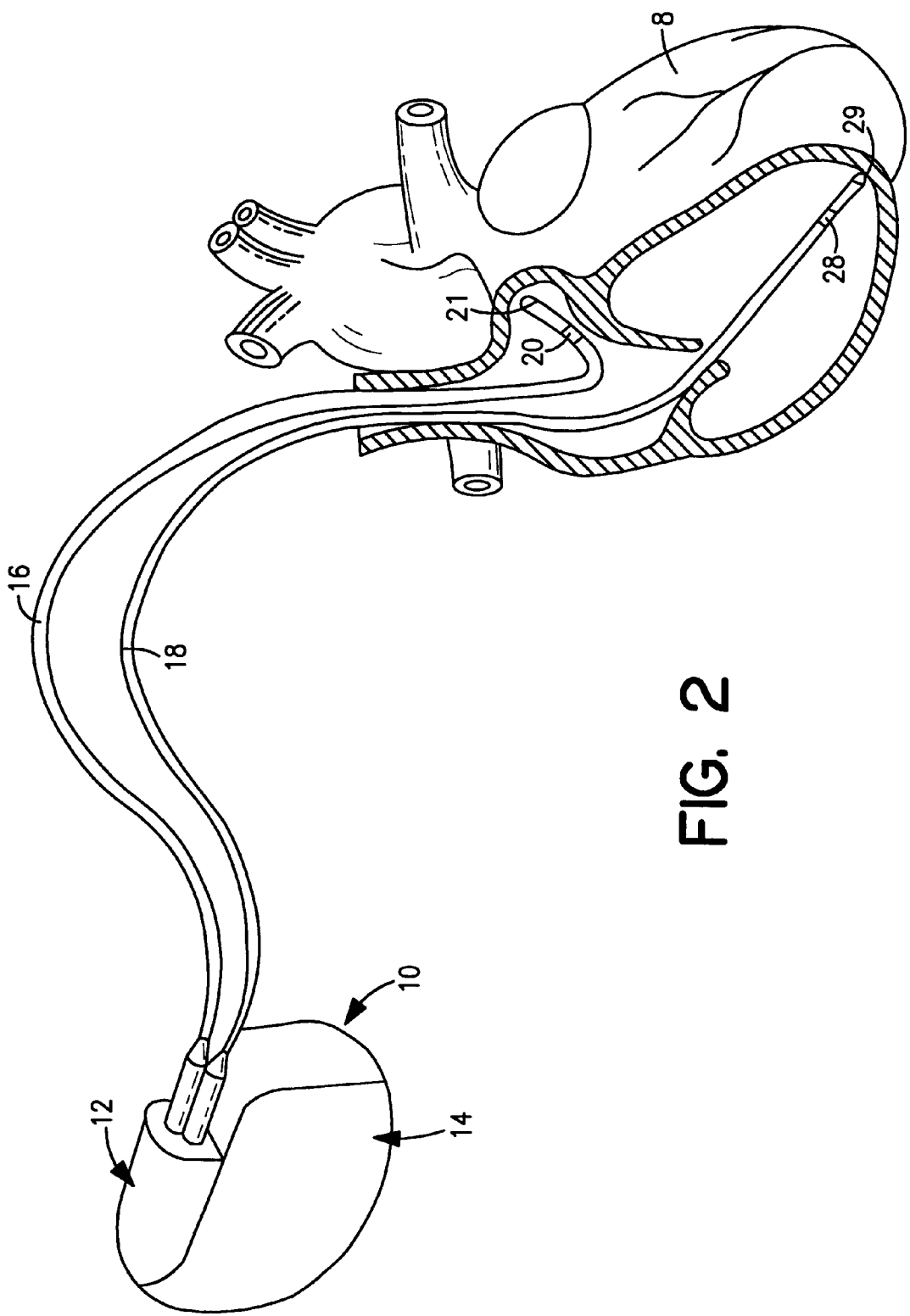
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
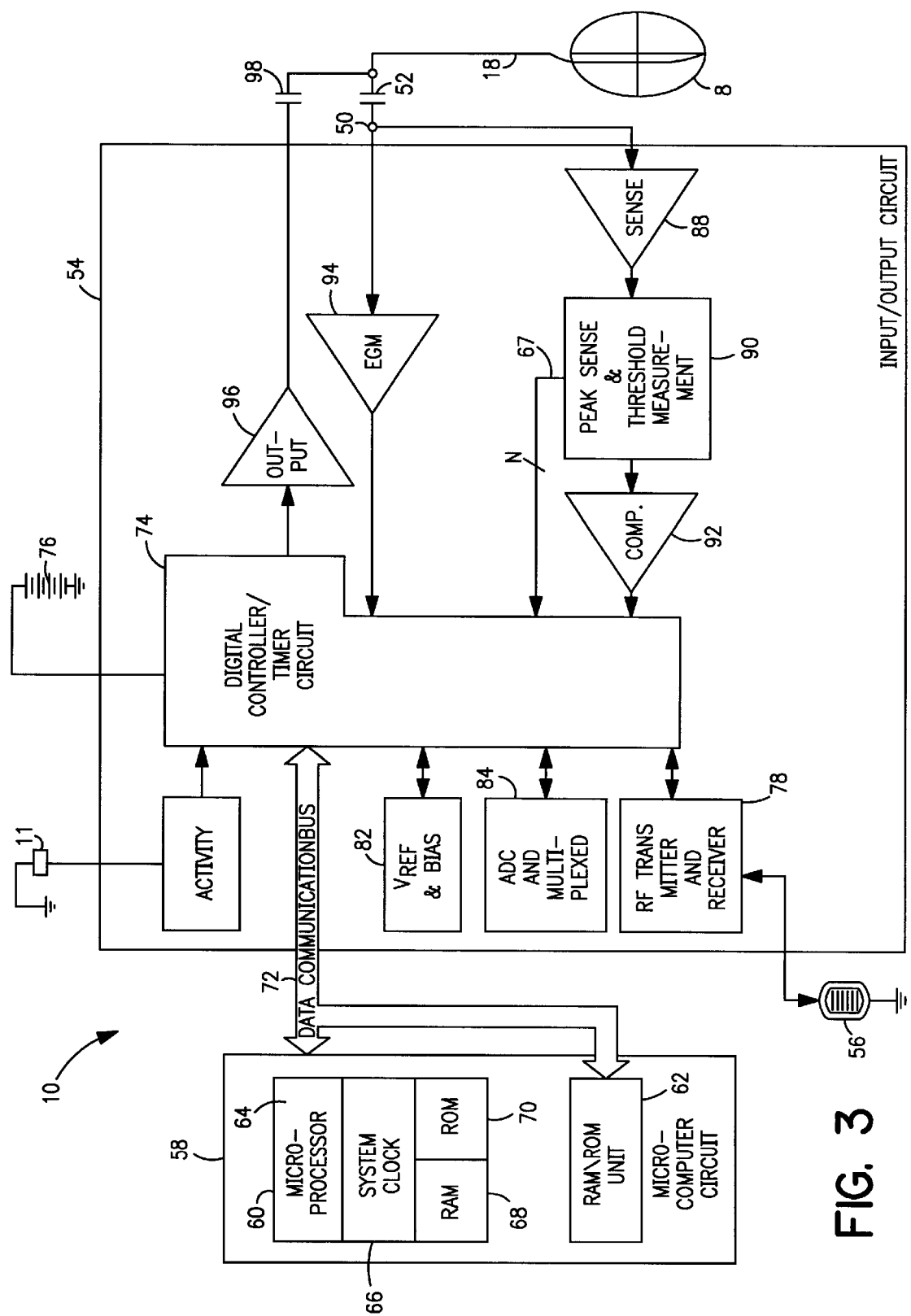
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and it is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Patent No. 4,821,723 to Baker et al., all hereby incorporated by reference herein, each in its respective entirety.

Figure 4:
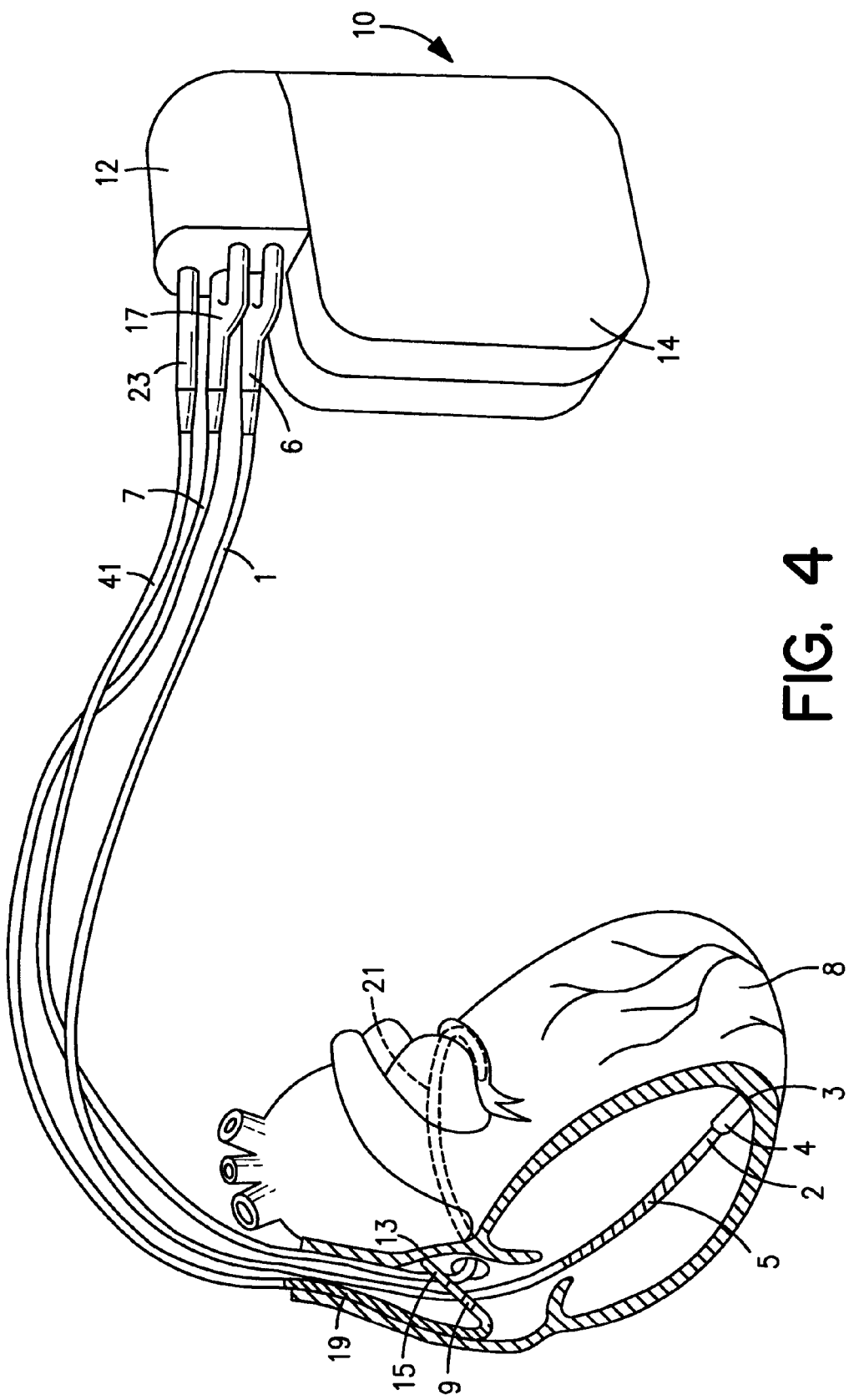
FIG. 4 is a graphic representation of an embodiment of this invention showing an implantable PCD device interconnected with a heart, the system of this embodiment providing pacing, cardioversion and defibrillation.
Figure 5:
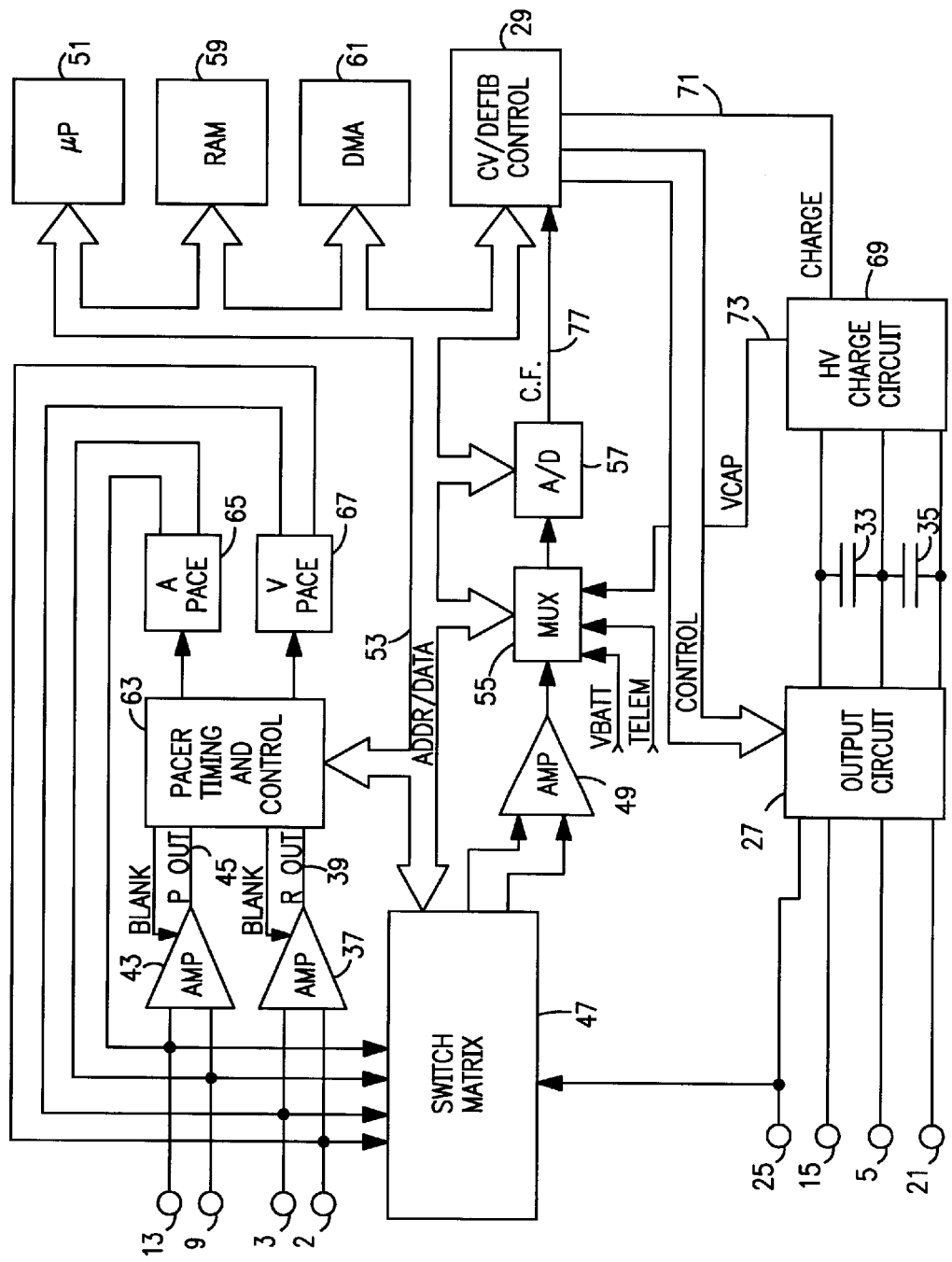
FIG. 5 is a functional schematic diagram of an implantable PCD embodiment of this invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 that carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
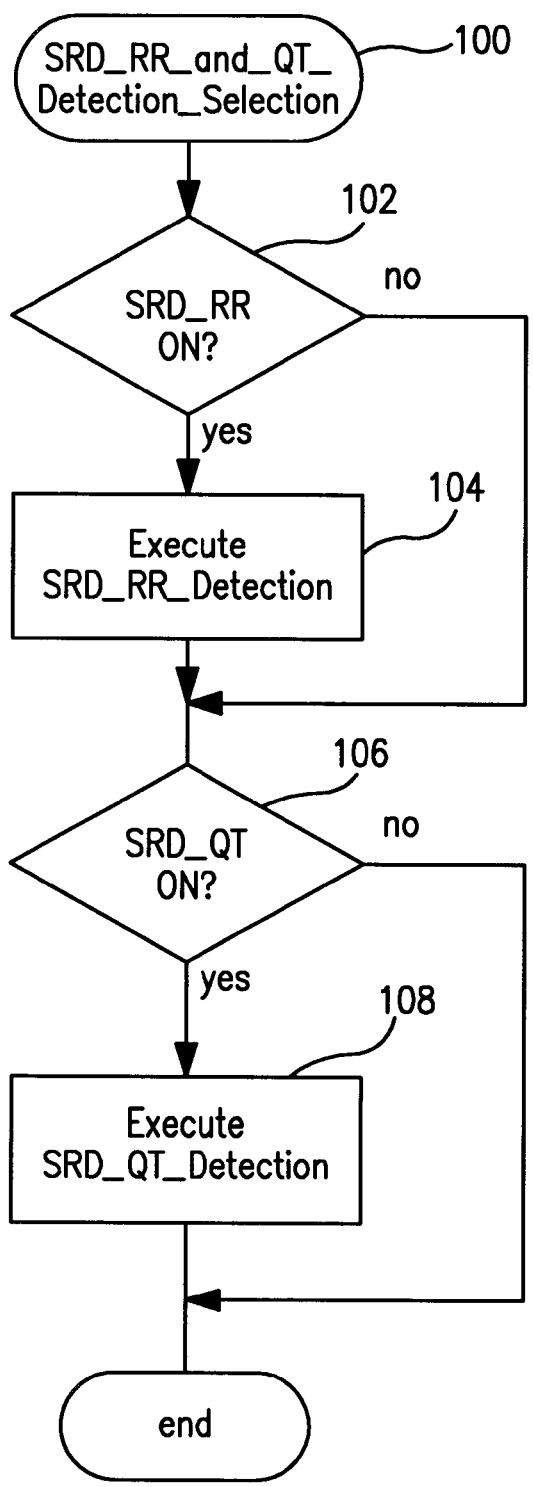
FIG. 6 is a flow diagram that illustrates which detection algorithms are utilized, depending upon selection by the patient's physician.

FIG. 6 illustrates the manner of selecting which of the SRD algorithms are run, in accordance with a preferred embodiment of this invention. The Detection_Selection algorithm 100 is entered every cycle and at 102 it is determined whether the SRD_RR algorithm is programmed on. The SRD_RR algorithm is programmable on or off by the physician. If it is programmed on, then the pacemaker goes to block 104 and executes the SRD_RR_Detection routine. This algorithm determines SRD solely on the basis of rate variations, e.g., drops in rate that exceed predetermined criteria. If this algorithm detects SRD, then a flag SRD_RR_Detected is set TRUE. Details of a preferred embodiment of this detection routine are set forth in the referenced U.S. Pat. No. 5,991,659. Other routines for examining drops in rate and determining when they are to be classified "sudden" are within the scope of this invention. If SRD_RR is not programmed on, the pacemaker branches directly to block 106, where it is determined whether the SRD_QT algorithm has been programmed on. If no, the routine exits. However, if it is programmed on, then the SRD_QT_Detection routine is executed, to detect whether variations in QT indicate the onset of SRD. Details of this routine are set forth in FIGS. 7A and 7B. Thus, if SRD detection based on shortening of QTc is to be used, the SRD_QT_Detection algorithm, or switch, has to be programmed on. If SRD is to be detected also on the basis of rate, the physician must program on the SRD_RR algorithm. If both detection algorithms are to be used, both switches are programmed on.

Figure 7A:
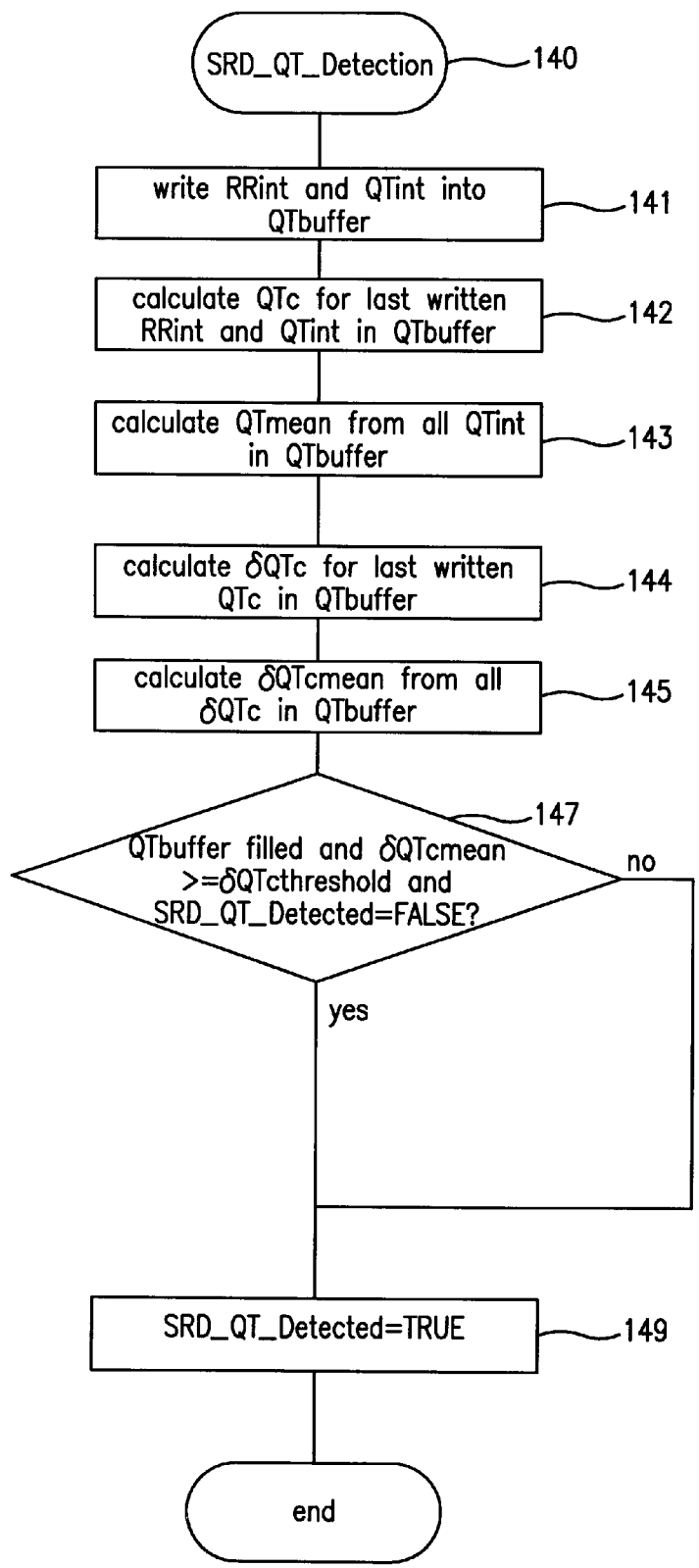
FIG. 7A is a flow diagram illustrating the primary steps taken by a preferred algorithm of this invention that detects SRD on the basis of differential changes in QTc.

FIG. 7A illustrates a flow diagram for an algorithm designed to detect SRD, and the onset of NMS, by evaluating differential changes in QTc. The SRD_QT_Detection algorithm 140 is run every cycle, when SRD_QT (shown in 106 of FIG. 6) programmed on. When this algorithm is initially switched on, the QT buffer is initialized. Each cycle, the pacemaker or other device obtains the RR interval and QT interval, and at 141 the RRint and QTint data is written into a QT buffer. The buffer may contain a variable amount of data, e.g. 5 to 8 pairs of RRint and QTint data. The circular buffer may also be time stamped, so that it can be downloaded later for evaluation by a physician. At 142, a value of QTc is calculated each time a new value for RRint and QTint is written into the QT buffer. This QTc value is also written into the QT buffer. As is known, there are different formulae in use for calculation of QTc. For the purposes of illustrating the invention the Bazett formula is used, namely QTc=QT√RR, where the QT and RR interval values are in seconds. However, the other formulas in use can likewise be utilized within the scope of this invention.

At 143, the algorithm calculates QTmean from the QT interval data contained in the QT buffer. The value of QTmean is used to set a limit on how short the escape interval can be made, to prevent pacing in the T wave. This step includes setting a minimum value of the escape interval to QTmean+n ms, where n is a programmable value selected to provide a safety factor for safe pacing. At 144, each time that a value of QTc is stored in the QT buffer, a differential value, δQTc is calculated. This is done by subtracting from each value of QTc the value of the just prior measurement of QTc. This calculated value of δQtc is also written into the circular QT buffer. Then, at 145, the algorithm calculates δQTcmean the mean value of δQTc from all of the calculated values of δQTc in the QT buffer. At 147, the calculated value QTcmean is compared with a programmable threshold value shown as δQTcthreshold. It is to be recalled that, for onset of NMS, the normal prolongation of QT interval is not found at lower rates, and as a consequence QTc decreases. While δQTc becomes negative, the absolute value of δQTcmean will increase in a patient with onset of NMS. Consequently, if δQTcmean is equal to or greater than the programmed threshold, this indicates onset of NMS. Comparing in block 147 is allowed only if the circular QT buffer is filled entirely. Also, if SRD_QT_Detected is not FALSE (it is set TRUE) the routine must exit so that a running intervention therapy can not be restarted. If these conditions are met, the routine goes to 149 and sets SRD_QT_Detected to be TRUE.

Figure 7B:
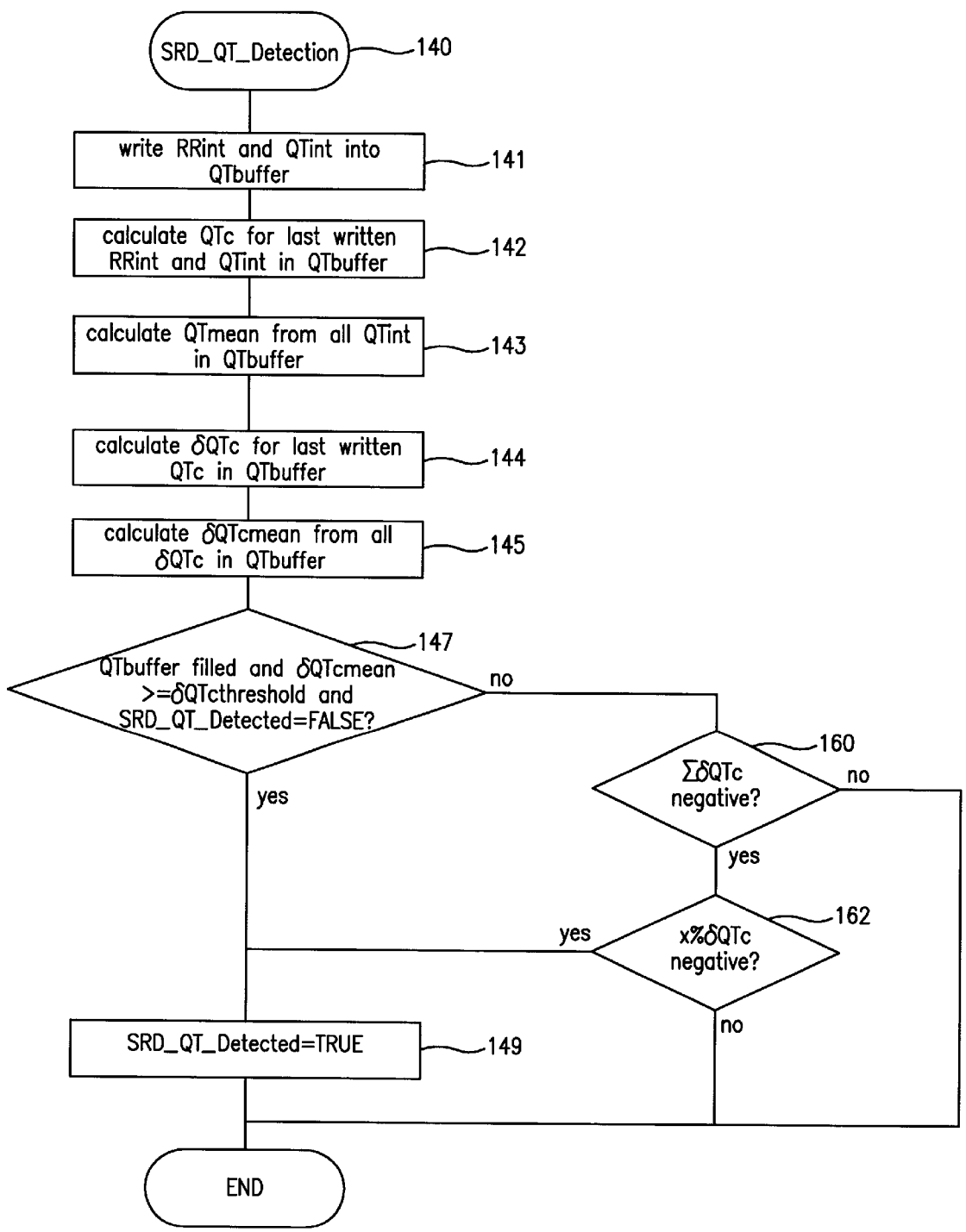
FIG. 7B illustrates a variation of the flow diagram of FIG. 7A in which there is incorporated another sequence of steps for determining when QT behavior indicates onset of SRD.

It is to be observed that other calculations of QT variations can be made within the scope of this invention. Calculating differential values of QTc is preferred, since NMS is characterized by very little prolongation of QT corresponding to longer RR intervals. A variation of the SRD_QT_Detection algorithm is shown in FIG. 7B. If at 147 the QT buffer is found to be filled and SRD_QT_Detected is False and δQtcmean is not equal to or greater than δQtcthreshold, the algorithm goes on to determine at 160 whether the sum of all δQTc in the QT buffer is negative. If so, at 162 the algorithm also checks to see if a predetermined percentage of the δQTc values in the buffer are negative. If both these criteria are met, this means that QTc is dropping, indicating the likelihood of NMS. The algorithm proceeds to 149 and sets SRD_QT_Detected= TRUE. Other variations of using QT to detect SRD, by comparing QT or QTc behavior to predetermined reference criteria, are within the scope of the invention. For example, in FIG. 7A the test for detection at block 147 may include determining that δQtcmean is negative.

Figure 8:
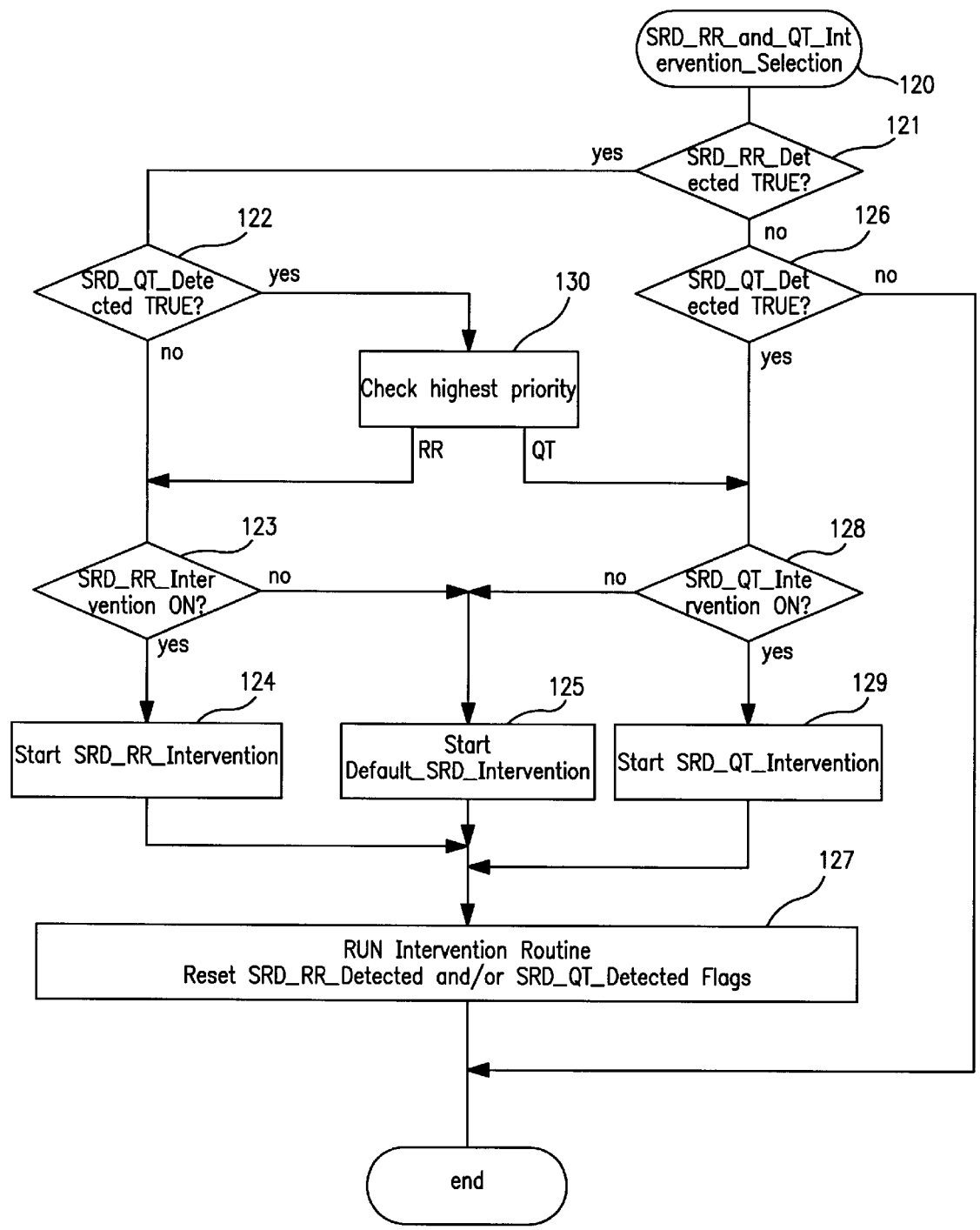
FIG. 8 is a flow diagram illustrating the manner of choosing what intervention pacing therapy is selected in the event of SRD detection.

The intervention selection routine 120 is illustrated in FIG. 8. This routine is entered every cycle as long as none of the intervention therapies is running. At 121, it is determined whether SRD_RR_Detected has been set TRUE, meaning that this routine has been run and has detected SRD. If yes, the routine goes to 122 and determines whether SRD_QT_Detected is also TRUE. If no, the algorithm goes to 123 and determines whether SRD_RR_Intervention is programmed on. If it is programmed on, this means that an RR pacing intervention therapy is desired, and the pacemaker goes to block 124 and starts SRD_RR_Intervention. This intervention may suitably be as illustrated in the referenced U.S. Pat. No. 5,991,659. However, if at 123 this particular intervention is not programmed on, the pacemaker goes to block 125 and starts a default intervention therapy, shown as Default_SRD_Intervention. The intervention therapies of blocks 124 and block 125 may differ, for example, by the programmed intervention rate, the rate of flywheel deceleration, and whether or not recovery hysteresis is employed, all of which is illustrated in the referenced patent. The selected intervention therapy is run at block 127, and after the therapy is completed the corresponding flag or flags SRD_RR_Detected and/or SRD_OT_Detected are reset to FALSE.

Returning to 122, if SRD_RR_Detected is set TRUE, then the routine goes to block 130 and checks the highest priority. This is programmable, and determines whether, when both the rate and QT algorithms detect TRUE, an RR or QT intervention response is desired. If RR is programmed as the highest priority, the routine goes to 123. If QT is the highest priority, the routine goes to 128. Going back to block 121, if the rate algorithm has not detected SRD, the algorithm goes to 126 and looks for the outcome of SRD_QT_ Detection. If this is not detected true, then there has been no SRD detection, and the routine exits. However, if SRD_ QT_Detected is set TRUE, the routine goes to 128 and determines whether the SRD_QT_Intervention is set ON. If no, the routine branches to block 125 to start the Default_ SRD_Intervention therapy. However, if yes, the routine goes to block 129, and starts a different intervention, namely SRD_QT_Intervention. The intervention therapies are run, and when they are finished the flags SRD_RR_Detected and SRD_QT_Detected are reset to false.

The preceding specific embodiments are illustrative of the practice of the invention. It is to be understood, therefore, that other expedients known to those skilled in the art or disclosed herein, may be employed without departing from the invention or the scope of the appended claims. Likewise, while the preferred embodiments of algorithms for detecting SRD based on QT have been disclosed, other criteria can be used for detecting when changes in QT indicate onset of SRD. The QT detection scheme is most easily carried out with a rate control pacemaker that uses a QT sensor, for which QT is already available each cycle. See U.S. Pat. Nos. 4,228,803 and 4,972,834, each incorporated herein by reference in its entirety. However, measurement of QT is within the state of the art for any other type of implanted cardiac device. So also a non-rate responsive device with T-wave amplifier can be used. The present invention is also not limited to any particular combination of hardware and software per se, but may find further application with any form of software supplementing hardware. The present invention further includes within its scope methods of making and using the medical systems and algorithms described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable pacing system having a pacemaker device and a lead that interconnects a patient's heart and said device, said device comprising:
   sensing means for sensing ventricular signals connected from the patient's bean;
   rate means for determining patient heart rate from sensed signals;
   QT means for determining a measure of the QT interval from said sensed signals;
   differential means for determining and storing differential changes in said QT measure from beat to beat;
   analysis means for determining when said differential changes indicate the onset of SRD; and
   intervention means for controlling said pacemaker device to pace said patient with intervening pacing pulses in response to a said indication of onset of SRD.

2. The system as described in claim 1, wherein said QT means comprises means for determining QTc for each said sensed signal and first storage means for storing QTc corresponding to each sensed signal, and wherein said analysis means comprises comparison means for comparing the trend of QTc with stored QTc data.

3. The system as described in claim 2, wherein said differential means comprises buffer means for storing n values of said differential changes and means for calculating a representation of said n values.

4. The system as described in claim 3, wherein said analysis means comprises threshold means for storing a differential QT threshold value, and comparing means for determining when said representation exceeds said threshold.

5. The system as described in claim 1, comprising QT(RR) storage means for storing values of QT and heart rate (RR) corresponding to each said signal, and time means for storing the time corresponding to at least periodic pairs of said QT and RR values.

6. The system as described in claim 5, said analysis means comprising means for determining when said differential changes represent negative changes.

7. The system as described in claim 5, comprising ref bronco means for storing reference QTc data, and wherein said analysis means comprises comparison means for comparing values of QTc with said reference data for the current heart rate.

8. The system as described in claim 7, wherein said analysis means comprises means for determining when stored values of QTc are negative.

9. The system as described in claim 1, wherein said device comprises a first detection algorithm for detecting onset of SRD based on QT interval, and a second detection algorithm for detecting onset of SRD based on rate changes.

10. The system as described in claim 9, comprising intervention control means for enabling said intervention means only when both said first and second algorithms have detected onset of SRD.

11. The system as described in claim 10, wherein said intervention means comprises a plurality of intervention control algorithms, and selection means for selecting one of said plurality of intervention control algorithms.

12. The system as described in claim 11, comprising detection selection means for selecting either one or both of said detection algorithms to be operative.

13. The system as described in claim 1, comprising plural detection algorithms for detecting SRD based on respective different parameters derived from said signals, plural intervention algorithms for providing a plurality of respective different intervention algorithms for controlling pacing intervention, and selection means for selecting operative ones of said detection algorithms and an operative intervention algorithm.

14. An implantable medical system having a pacing device and a lead system interconnecting said device with the heart of a patient, said device comprising:
   signal means for sensing cardiac signals from said patient;
   first rate drop detection means for determining a first parameter from said signals and detecting sudden rate drop as a function of variations of said first parameter;
   second rate drop detection means for determining a second parameter from said signals and detecting sudden rate drop as a function of variations of said second parameter; and
   intervention pacing means for pacing said heart with intervention pacing when at least one of said first and second detection means detects sudden rate drop, wherein said intervention means comprises a plurality of intervention algorithms for controlling intervention pacing, and selection means for selecting one of said algorithms depending on which of said first and second detection means detects sudden rate drop.

15. The system as described in claim 14, wherein said first rate drop means comprises RR means for determining heartbeat rate and SRD_RR means for detecting sudden rate drop as a function of variations of patient heartbeat rate; and said second rate drop means comprises QT means for determining a measure of QT and SRD_QT means for detecting sudden rate drop as a function of said QT measure.

16. The system as described in claim 15, wherein one of said intervention algorithms is an SRD_QT algorithm adapted to treat sudden rate drop manifested by abnormal QT, and said selection moans comprises means for selecting said SRD_QT algorithm when said second rate drop means detects sudden rate drop.

17. The system as described in claim 16, wherein said QT means comprises means for determining QTc each heartbeat and said SRD_QT algorithm comprises differential means for determining and storing differential changes in QTc from beat to beat.

18. The system as described in claim 17, wherein said differential means comprises a buffer for storing n values of said differential changes in QTc and calculating means fir calculating a representation of said n values.

19. The system as described in claim 18, wherein said calculating means comprises means for calculating the mean value of said n values.

20. The system as described in claim 18, comprising comparison means for comparing said mean value with a predetermined threshold.

21. The system as described in claim 18, comprising means for determining when said differential changes are negative.

22. A method of determining the onset of SRD in a patient having an implanted cardiac device, comprising:

storing in said device predetermined criteria relating to normal beat-to-beat behavior of QT;

obtaining measures of QT for patient heartbeats;

comparing said measures with said criteria;

determining the onset of SRD as a function of said comparing; and calculating a value of OTc for each said patient heartbeat, and determining variations in said OTc values.

23. The method as described in claim 22, comprising storing a threshold value of ∂QTc, determining differences of QTc for consecutive values of QTc, and comparing said differences against said stored value of ∂QTc.

24. The method as described in claim 23, comprising calculating a value of QTmean for each patient heartbeat, and limiting the escape interval for the next cardiac cycle to QTmean+n ms.

25. The method as described in claim 23, comprising storing a predetermined number of consecutive values of QTc in a buffer, and determining each cardiac cycle whether the change in QTc from the earliest to the latest of said QTc values is negative.

26. The method as described in claim 22, comprising storing a rate-based algorithm for detecting SRD in said device, and running said rate-base algorithm each cardiac cycle.

27. The method as described in claim 26, comprising storing a plurality of intervention pacing therapy control algorithms in said device, and selecting one of said control algorithms when SRD is detected.

28. The method as described in claim 27, comprising programming a priority for selecting one of said control algorithms.

29. A method of detecting and treating sudden rate drop in a patient, utilizing an implanted medical device system, comprising:

storing in said system a plurality of sudden rate drop detection algorithms, and enabling and operating at least one of said algorithms;

storing in said system a plurality of intervention pacing routines;

providing an indication when sudden rate drop is detected by a said detection algorithm;

selecting one of said intervention pacing routines in response to a said indication; and treating said patient with intervention pacing controlled by said selected routine.

30. The method as described in claim 29, comprising storing a QT-based detection algorithm and at least one other detection algorithm.

31. The method as described in claim 30, comprising using an external programming said implanted device to enable both of said detection algorithms, and operating both of said algorithms.

32. The method as described in claim 31, comprising programming said device to prioritize the selection of a said intervention pacing routine when both of said detection algorithms indicate detection of sudden rate drop.

33. The method as described in claim 31, comprising storing at least three intervention pacing routines, and selecting one of said intervention pacing routines as a function of which detection algorithm or algorithms indicate detection of sudden rate drop.

34. The method as described in claim 30, comprising storing a rate-based detection algorithm.

35. The method as described in claim 34, comprising storing a QT intervention routine and a rate (RR) intervention routine.

36. The method as described in claim 35, comprising programming each of said intervention routines to be on or off.

37. The method as described in claim 35, comprising selecting said RR intervention pacing routine when only the rate-based algorithm indicates detection of sudden rate drop, and selecting said QT intervention pacing routine when only the QT-based algorithm indicates detection of sudden rate drop.

38. The method as described in claim 37, comprising enabling and operating each of said detection algorithms and programming each of said intervention routines to be on.

39. The method as described in claim 38, wherein the step of operating said QT algorithm comprising determining QTc each patient cardiac cycle, and obtaining a measure of how QTc differs over a predetermined number of cycles.

40. The method as described in claim 39, comprising calculating ∂QTc each cycle and the mean value of ∂QTc for said predetermined number of cycles and comparing said mean value with a ∂QTc threshold reference.

41. The method as described in claim 40, comprising determining when a said ∂QTc value is negative, and determining whether the sum of said ∂QTc values over said predetermined number of cycles is negative.

42. The method as described in claim 40, comprising indicating detection of SRD when said mean value is greater than said threshold reference.

43. The method as described in claim 42, further comprising determining when at least a predetermined percentage of said ∂QTc values within said predetermined number of cycles is negative.

44. The method as described in claim 30, comprising determining and storing a measure of QT each cycle, calculating a measure of the change of said QT measure over a predetermined number of cycles, and comparing said change measure with a predetermined threshold.

45. The method as described in claim 44, comprising programming a selected one or ones of said intervention routines to be on.

46. The method as described in claim 44, wherein said determining step comprises determining a measure of QT that is substantially independent of rate.

47. The method as described in claim 46, comprising determining QTc each cycle, calculating ∂QTc each cycle, and calculating the mean value of ∂QTc over said predetermined number of cycles.

48. The method as described in claim 47, comprising comparing said mean value of ∂QTc with a threshold reference value of ∂QTc each cycle.

49. The method as described in claim 47, comprising indicating SRD when said mean value is greater than said threshold reference value.

50. The method as described in claim 48, comprising indicating SRD when said mean value is negative and greater than said threshold reference value.

51. An implantable medical system having a pacing device and a lead system interconnecting said device with the heart of a patient, said device comprising:

signal means for sensing cardiac signals from said patient;

first rate drop detection means fix determining a first parameter from said signals and detecting sudden rate drop as a function of variations of said first parameter;

second rate drop detection means for determining a second parameter from said signals and detecting sudden rate drop as a function of variations of said second parameter, and intervention pacing means for pacing said heart with intervention pacing when a prioritized variable detects sudden rate drop.

52. The system as described in claim 51, further comprising prioritizing detection of sudden rate drop as a function of either the first parameter or the second parameter based upon variations of said first parameter and said second parameter to establish a prioritized parameter based upon variations of said first parameter and said second parameter.

53. The system as described in claim 51, wherein said first rate drop means comprises RR moans for determining heartbeat rate and SRD_RR means for detecting sudden rate drop as a function of variations of patient heartbeat rate; and said second rate drop means comprises QT means for determining a measure of QT and SRD_QT means for detecting sudden rate drop as a function of said QT measure.

* * * * *